United States Patent [19]

Spitzer et al.

[11] 4,243,588
[45] Jan. 6, 1981

[54] PROCESS FOR NOVEL OXAZOLINOAZETIDINONES

[75] Inventors: Wayne A. Spitzer; Theodore Goodson, Jr., both of Indianapolis, Ind.

[73] Assignee: Eli Lilly and Company, Indianapolis, Ind.

[21] Appl. No.: 50,041

[22] Filed: Jun. 19, 1979

[51] Int. Cl.$^3$ .......................................... C07D 498/04
[52] U.S. Cl. ................................................. 260/245.4
[58] Field of Search ......................... 260/307 F, 245.4

[56] References Cited

U.S. PATENT DOCUMENTS

| | | | |
|---|---|---|---|
| 3,948,927 | 4/1976 | Wolfe | 260/307 F |
| 3,950,352 | 4/1976 | Wolfe | 260/307 F |
| 4,013,653 | 3/1977 | Wolfe | 260/244 |
| 4,071,512 | 1/1978 | Wolfe | 260/239 A |
| 4,158,004 | 6/1979 | Koppel et al. | 260/307 F |
| 4,159,984 | 7/1979 | Yoshioka et al. | 260/307 F |

FOREIGN PATENT DOCUMENTS 863700 5/1978 Belgium .
863998 5/1978 Belgium .

OTHER PUBLICATIONS

Okazaki et al., Chem. Abs., 73, 44676m, (1970).
Cooper et al., Chem. Abs., 89, 215396g, (1978).

*Primary Examiner*—Mark L. Berch
*Attorney, Agent, or Firm*—Steven R. Lammert; Arthur R. Whale

[57] ABSTRACT

Novel oxazolinoazetidinone intermediates are prepared by cyclizing 2-chloroazetidinones with lead difluoride in dimethyl sulfoxide. The oxazolinoazetidinone products are useful as intermediates in the preparation of oxygen analogues of penicillins.

5 Claims, No Drawings

PROCESS FOR NOVEL OXAZOLINOAZETIDINONES

BACKGROUND AND SUMMARY OF THE INVENTION

Recently chemistry in the research area of beta-lactam antibiotics has become substantially more complex. Many scientists have directed their efforts to the preparation of novel bicyclic beta-lactam antibiotics differing from naturally occuring penicillins and cephalosporins not only in the nature of the side chain group or the C-3 group in cephalosporins but also in the nature of the ring-hetero atom (i.e. oxygen, nitrogen or even carbon in place of sulfur) and in the positioning of the ring-hetero atom. Of course, in the continuing search for novel beta-lactam antibiotic compounds, researchers have prepared a wide variety of mono and bicyclic beta-lactam containing intermediates. Such intermediates have been prepared either by totally synthetic routes or by molecular modification of penicillins or cephalosporins.

The present invention is directed to novel beta-lactam containing bicyclic intermediates and to a process for their preparation. More particularly the present invention is directed to certain oxazolinoazetidinones of the formula

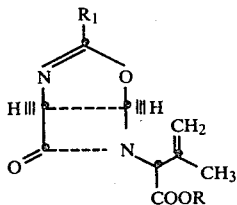

which are useful in the preparation of oxygen analogues of penicillins. The oxazolinoazetidinone intermediates of the present invention are prepared from 2-chloroazetidinones.

DETAILED DESCRIPTION OF THE INVENTION

The present invention is directed to oxazolinoazetidinones of the formula

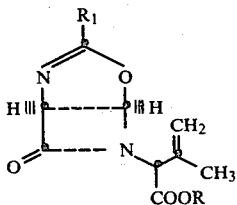

wherein R is hydrogen or a carboxylic acid protecting group and $R_1$ is (a) hydrogen, $C_1$–$C_4$ alkyl or halo($C_1$–$C_4$ alkyl);

(b) a group $R_6$ wherein $R_6$ is phenyl or phenyl substituted by 1 or 2 groups selected from the group consisting of fluoro, chloro, bromo, iodo, nitro, cyano, $C_1$–$C_4$ alkyl, $C_1$–$C_4$ alkoxy, protected hydroxy, carbamyl, trifluoromethyl and methanesulfonamido;

(c) a group of the formula $R_6(O)_mCH_2-$ wherein m is 1 or 0 and $R_6$ is as defined above;

(d) a group of the formula $R_{6a}CH_2-$ wherein $R_{6a}$ is cyclohexadienyl, 2-furyl, 2-thienyl, or 3-thienyl; or (e) a group of the formula—COOR wherein R is as defined above.

The term "protected hydroxy" has reference to the readily cleavable groups formed with an hydroxyl group such as the formyloxy group, the chloroacetoxy group, the benzyloxy group, the benzhydryloxy group, the trityloxy group, the 4-nitrobenzyloxy group, the trimethylsilyloxy group, the phenacyloxy group, the tert-butoxy group, the methoxymethoxy group, the tetrahydropyranyloxy group, and the like. Other hydroxy protecting groups, including those described by C. B. Reese in *Protective Groups in Organic Chemistry*, supra, Chapter 3 shall be considered as within the term "protected hydroxy" as used herein.

The term "carboxylic acid protecting group" has reference to the commonly used carboxylic acid protecting groups employed to block or protect the carboxylic acid functionality while reactions involving other functional sites of the compound are carried out. Such carboxy protecting groups are noted for their ease of cleavage by hydrolytic or by hydrogenolytic methods to the corresponding carboxylic acid. Examples of carboxylic acid ester protecting groups include methyl, tert-butyl, benzyl, 4-methoxybenzyl, $C_2$–$C_6$ alkanoyloxymethyl, 2-iodoethyl, 4-nitrobenzyl, diphenylmethyl (benzhydryl), phenacyl, 4-halophenacyl, dimethylallyl, 2,2,2-trichloroethyl, tri($C_1$–$C_3$ alkyl)silyl, succinimidomethyl and like ester forming moieties. In addition to ester protection of carboxy groups, such groups can also be protected as the mixed anhydride, such as that formed with acetyl chloride, propionyl chloride, isobutyryl chloride and like acid chlorides in the presence of a tertiary amine base. Other known carboxy protecting groups such as those described by E. Haslam in *Protective Groups in Organic Chemistry*, supra, Chapter 5, shall be recognized as suitable. The ester forming protecting groups are preferred. The nature of such ester forming groups is not critical.

In the foregoing definitions hydroxy and carboxy protecting groups are not exhaustively defined. The function of such groups is to protect the reactive functional groups during the preparative steps and then to be removed at some later point in time without disrupting the remainder of the molecule. Many protecting groups are known in the art, and the use of other protecting groups not specifically referred to hereinabove are equally applicable.

Exemplary of the $R_1$ groups in accordance with the above definition are hydrogen, methyl, ethyl, sec-butyl, tert-butyl, chloromethyl, bromomethyl, 2-iodoethyl, 2-fluoropropyl, phenyl, 2-bromophenyl, 4-chlorophenyl, 4-methoxyphenyl, p-tolyl, o-tolyl, 4-benzyloxyphenyl, 3-carbamylphenyl, 4-chloro-3-cyanophenyl, 4-methoxy-2-tolyl, 4-trifluoromethylphenyl, benzyl, 4-methoxybenzyl, 4-iodobenzyl, 3-methanesulfonamidobenzyl, 3-nitrobenzyl, 3-chloro-4-benzyloxybenzyl, 2-ethylbenzyl, phenoxymethyl, 4-bromophenoxymethyl, 2-methoxyphenoxymethyl, 4-tolyloxymethyl, 4-chlorophenoxymethyl, 4-carbamylphenoxymethyl, 3-chloro-4-ethoxyphenoxymethyl and like groups. $R_1$ can also be 2-furylmethyl, 2-thienylmethyl, 3-thienylmethyl, cyclohexadienylmethyl, carbomethoxy, 4-nitrobenzyloxycarbonyl, 4-methoxybenzyoxycarbonyl, tert-butoxycarbonyl, benzhydryloxycarbonyl and the like. Preferred $R_1$ groups are phenyl, p-tolyl, benzyl and phenoxymethyl.

The present oxazolinoazetidinones are prepared from 2-chloroazetidinones of the formula

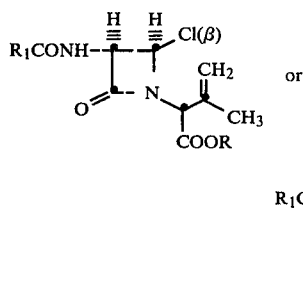  or

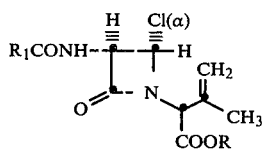

wherein R and $R_1$ as defined above, the general preparation of which is described in U.S. Pat. No. 4,013,653 issued Mar. 22, 1977. The 2-beta-chloroazetidinone represented in formula I are cyclized to the oxazolinoazetidinones of the present invention essentially in quantitative yield using lead difluoride in dimethyl sulfoxide. The cyclization reaction is typically conducted at ambient temperature, however the cyclization can be conducted at temperatures ranging from about 0° to about 60° C. A temperature of about 20° to about 30° C. is preferred.

The reaction mixture is typically heterogenous because lead fluoride has but marginal solubility in dimethyl sulfoxide. The present cyclization can be accomplished using from about 0.1 to about 2.0 molar equivalents of lead difluoride for each molar equivalent of chloroazetidinone starting material. Preferably about 1 to about 2 molar equivalent of lead fluoride is employed for each mole of chloroazetidinone. Usually the reaction is conducted by combining equal weights of the chloroazetidinone and lead fluoride in dimethyl sulfoxide at room temperature. At room temperature the reaction is complete in about 1 to 4 hours.

Alternatively the present oxazolinoazetidinones can be prepared from the 2-beta-chloroazetidinones (I) by reacting the 2-beta-chloroazetidinone with lithium chloride in acetone to provide a mixture of chloro azetidinones I and II and then chromatographing the mixture over silica gel. The 2-alpha-chloroazetidinone II cyclizes during chromatography over silica gel.

The oxazolineazetidinone compounds of the present invention are useful intermediates for the preparation of oxygen analogues of penicillins. Treatment of the present compounds with triethylamine in for example ethyl acetate, methylene chloride or chloroform, provides the corresponding α,β-unsaturated oxazolinoazetidinone compounds of the formula

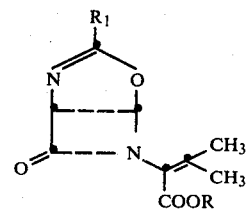

which can be converted to compounds of the formula

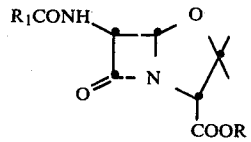

in either accordance with the teaching of U.S. Pat. Nos. 3,948,927 and 3,950,352 issued Apr. 6, 1976 and Apr. 13, 1976 respectively or in accordance with the teaching of U.S. Pat. No. 4,071,512 issued Jan. 31, 1978.

EXAMPLE 1 p-Nitrobenzyl 2(R)-3-methyl-2-[1S,5R)-3-phenoxymethyl-7-oxo-4-oxa-2,6-diazabicyclo[3.2.0]-hept-2-en-6-yl]-3-butenoate

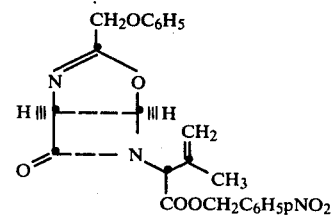

Lead fluoride (3 grams) is added to a solution of 3 grams of p-nitrobenzyl 2R-(3β-phenoxyacetamido-2-oxo-4β-chloroazetidin-1-yl)-3-methyl-3-butenoate in 30 ml of dimethyl sulfoxide. The suspension was stirred for 4 hours at room temperature. Ethyl acetate (100 ml) was added, and the resulting mixture was washed with saturated sodium chloride solution (3×150 ml). The organic layer was separated, dried over anhydrous magnesium sulfate and evaporated in vacuo to dryness to give a colorless gum. An nmr spectrum of the product showed it to be titled product.

nmr (CDCl$_3$) δ 1.78 (s, 3, CH$_3$), 4.73 (s, 2, C$_1$H$_5$OC$\underline{H}_2$), 4.9–5.1 (m, 4), 5.26 (s, 2, ester CH$_2$), 6.25 (d, 1, J=3.8 Hz) and 6.83–8.26 (m, 9, ArH).

We claim:

1. The process for preparing a compound of the formula

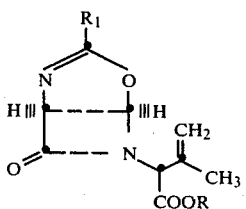

which comprises reacting a chloroazetidinone compound of the formula

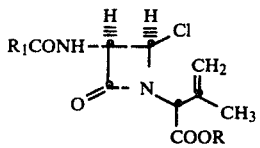

with lead difluoride in dimethyl sulfoxide at about 0° to about 60° C. wherein in the above formulas R is hydrogen or a carboxylic acid protecting group and $R_1$ is (a) hydrogen, $C_1$–$C_4$ alkyl or halo($C_1$–$C_4$ alkyl);

(b) a group $R_6$ wherein $R_6$ is phenyl or phenyl substituted by 1 or 2 groups selected from the group consisting of fluoro, chloro, bromo, iodo, nitro, cyano, $C_1$–$C_4$ alkyl, $C_1$–$C_4$ alkoxy, protected hydroxy, carbamyl, trifluoromethyl and methanesulfonamido;

(c) a group of the formula $$R_6(O)_mCH_2-$$

wherein m is 1 or 0 and $R_6$ is as defined above;

(d) a group of the formula $$R_{6a}CH_2-$$

wherein $R_{6a}$ is cyclohexadienyl, 2-furyl, 2-thienyl, or 3-thienyl; or (e) a group of the formula —COOR wherein R is as defined above.

2. The process of claim 1 wherein R is a carboxylic acid ester protecting group.

3. The process of claim 2 wherein from about 0.1 to about 2.0 molar equivalents of lead fluoride is employed for each mole of the chloroazetidinone.

4. The process of claim 3 wherein the process is carried out at a temperature of about 0° to about 60° C.

5. The process of claim 3 wherein $R_1$ is phenyl, p-tolyl, benzyl or phenoxymethyl.

* * * * *